(12) United States Patent
Molloy

(10) Patent No.: US 12,427,343 B2
(45) Date of Patent: Sep. 30, 2025

(54) CRADLE AND FEEDBACK MECHANISM FOR AUTOMATED DEVICE ALIGNMENT IN RADIATION THERAPY

(71) Applicant: UNIVERSITY OF KENTUCKY RESEARCH FOUNDATION, Lexington, KY (US)

(72) Inventor: Janelle A. Molloy, Nicholasville, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 193 days.

(21) Appl. No.: 18/283,410

(22) PCT Filed: Mar. 24, 2022

(86) PCT No.: PCT/US2022/021793
§ 371 (c)(1),
(2) Date: Sep. 21, 2023

(87) PCT Pub. No.: WO2022/204432
PCT Pub. Date: Sep. 29, 2022

(65) Prior Publication Data
US 2024/0173572 A1    May 30, 2024

Related U.S. Application Data

(60) Provisional application No. 63/165,397, filed on Mar. 24, 2021.

(51) Int. Cl.
*A61N 5/10* (2006.01)

(52) U.S. Cl.
CPC ......... *A61N 5/1075* (2013.01); *A61N 5/1067* (2013.01); *A61N 2005/1076* (2013.01)

(58) Field of Classification Search
CPC .............................. A61N 2005/1076
See application file for complete search history.

(56) References Cited

U.S. PATENT DOCUMENTS

| | | | |
|---|---|---|---|
| 2002/0181660 A1* | 12/2002 | Reinstein | A61N 5/1048 378/207 |
| 2005/0211889 A1 | 9/2005 | Varchena et al. | |
| 2007/0071176 A1* | 3/2007 | Main | A61N 5/1075 378/207 |
| 2007/0195922 A1* | 8/2007 | Mackie | G21K 1/046 378/4 |
| 2008/0144776 A1* | 6/2008 | Main | A61N 5/1075 378/163 |

(Continued)

*Primary Examiner* — Blake C Riddick
(74) *Attorney, Agent, or Firm* — Stites & Harbison PLLC; Warren D. Schickli

(57) ABSTRACT

An apparatus adapted for automated device alignment in radiation therapy quality assurance, includes a base, a rotation adjustment assembly supported on the base, a tilt adjustment assembly supported on the rotation adjustment assembly, a quality assurance device supported on a cradle of the tilt adjustment assembly, a position sensor adapted to provide accurate measurements of a current position of the cradle during cradle position adjustment, and a controller configured to control operation of the rotation adjustment assembly and the tilt adjustment assembly and receive data from the position sensor respecting the current position of the cradle.

20 Claims, 14 Drawing Sheets

(56) References Cited

U.S. PATENT DOCUMENTS

| | | | | |
|---|---|---|---|---|
| 2009/0003975 | A1* | 1/2009 | Kuduvalli | B25J 9/0084 |
| | | | | 901/19 |
| 2009/0225957 | A1* | 9/2009 | Varchena | A61N 5/1049 |
| | | | | 378/207 |
| 2011/0022360 | A1 | 1/2011 | Simon et al. | |
| 2011/0185503 | A1* | 8/2011 | Yan | A61N 5/1049 |
| | | | | 5/601 |
| 2014/0016759 | A1* | 1/2014 | Ngar | G05B 19/4015 |
| | | | | 378/207 |
| 2014/0267697 | A1* | 9/2014 | Wong | A61B 6/4216 |
| | | | | 348/135 |
| 2015/0036806 | A1* | 2/2015 | Wong | A61N 5/1075 |
| | | | | 378/207 |
| 2015/0316657 | A1* | 11/2015 | Ruschin | G01T 1/04 |
| | | | | 250/252.1 |
| 2016/0114190 | A1* | 4/2016 | Brown | A61B 6/584 |
| | | | | 378/205 |
| 2017/0225015 | A1* | 8/2017 | Thieme | A61B 6/4258 |
| 2017/0312547 | A1* | 11/2017 | Wong | A61N 5/1075 |
| 2018/0133508 | A1* | 5/2018 | Pearce | A61N 5/107 |
| 2018/0318609 | A1* | 11/2018 | Arican | A61N 5/1075 |
| 2019/0143145 | A1* | 5/2019 | Laurence, Jr. | A61B 34/10 |
| | | | | 600/1 |
| 2019/0175951 | A1* | 6/2019 | Yu | A61B 6/032 |
| 2020/0289853 | A1* | 9/2020 | Friedman | A61N 5/1064 |
| 2020/0359988 | A1* | 11/2020 | Woods | A61B 6/08 |
| 2021/0012507 | A1* | 1/2021 | Kapatoes | A61N 5/1071 |
| 2021/0228910 | A1* | 7/2021 | Subrahmanyam | A61N 5/1081 |
| 2021/0236855 | A1* | 8/2021 | Adamson | A61N 5/1045 |
| 2022/0001210 | A1* | 1/2022 | Letourneau | G16H 30/20 |
| 2022/0062659 | A1* | 3/2022 | Ansorge | G01T 1/2914 |
| 2023/0222670 | A1* | 7/2023 | Kapatoes | G06T 7/0012 |
| | | | | 378/65 |
| 2024/0066324 | A1* | 2/2024 | Alexander | A61N 5/1075 |
| 2024/0350832 | A1* | 10/2024 | Harper | A61N 5/1081 |

* cited by examiner

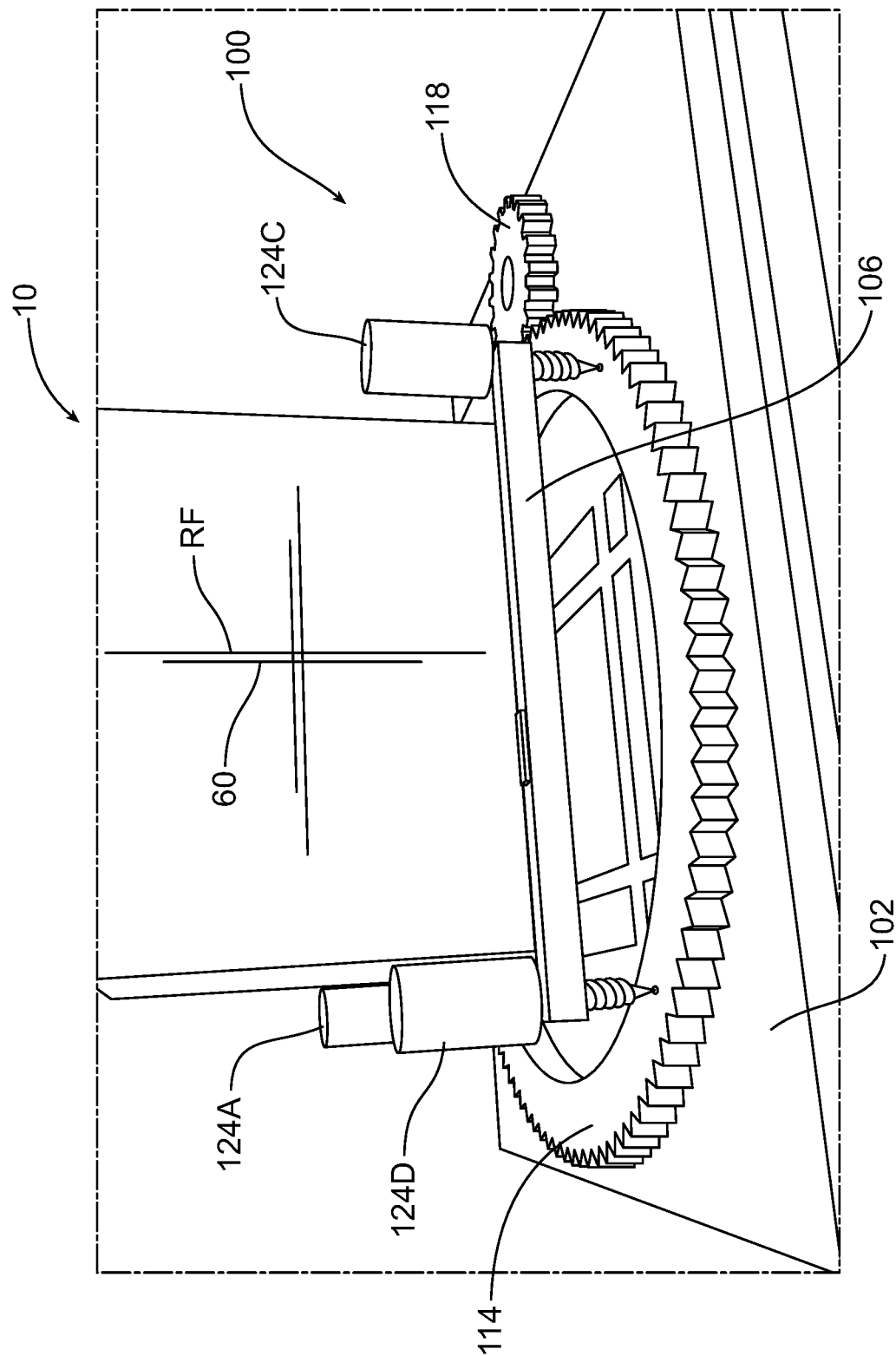

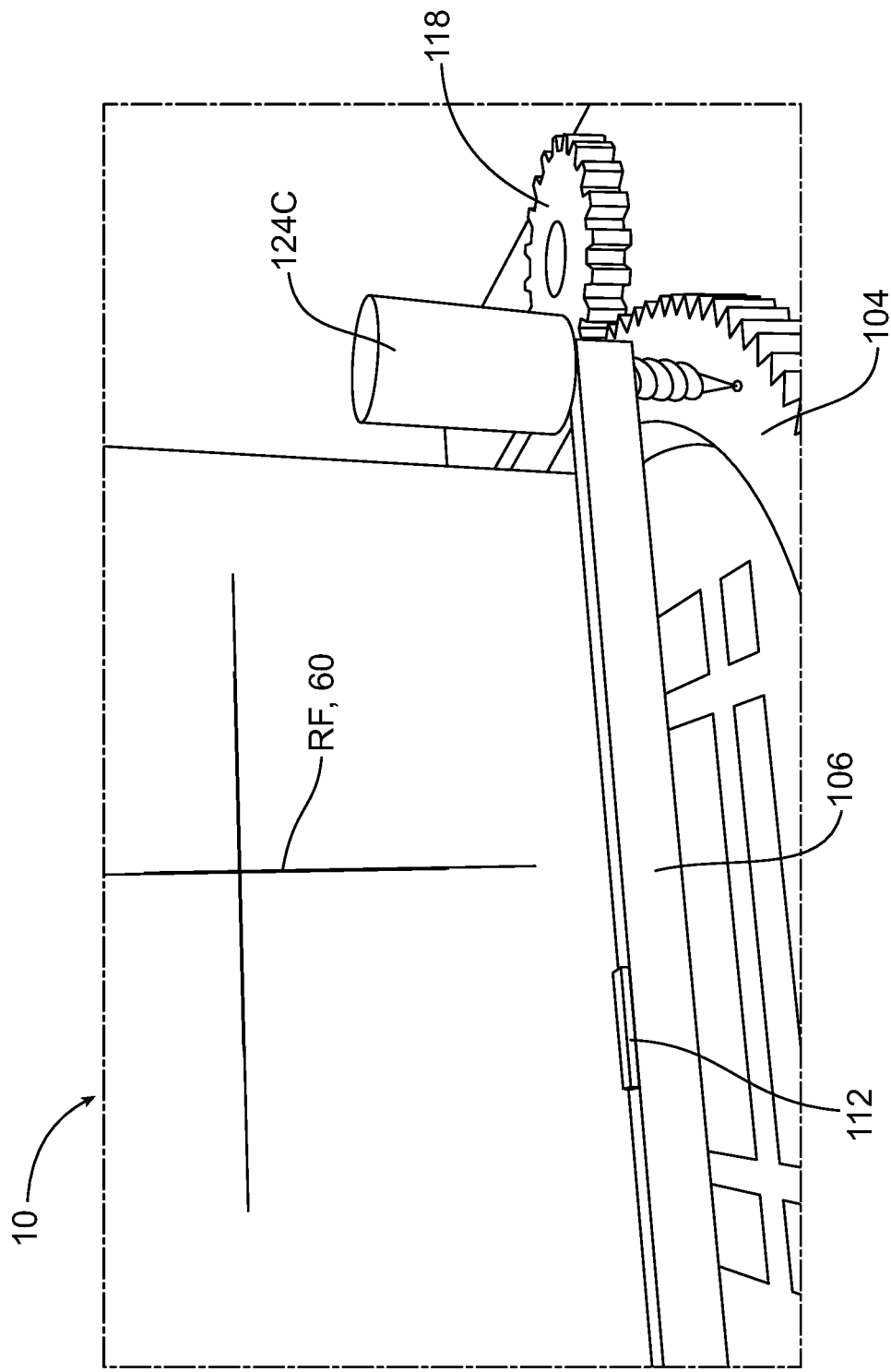

CRADLE AND FEEDBACK MECHANISM FOR AUTOMATED DEVICE ALIGNMENT IN RADIATION THERAPY

RELATED APPLICATION

This application is a §371 National State Application of PCT/US2022/021793 filed Mar. 24, 2022 which claims priority to U.S. Provisional Patent Application Ser. No. 63/165,397 filed on Mar. 24, 2021, which are hereby incorporated by reference in its entirety.

TECHNICAL FIELD

This document relates generally to the medical equipment field and, more particularly, to an apparatus adapted for automated quality assurance device alignment for radiation therapy quality assurance.

BACKGROUND

This document relates generally to a new and improved cradle and feedback apparatus designed to automatically reposition and change the angular orientation of a quality assurance device for radiotherapy on a medical accelerator. The quality assurance device is adapted for acquiring quality assurance measurements on medical linear accelerators used for radiation therapy of cancer patients. The quality assurance device is designed so that it is capable of acquiring comprehensive optical, radiation and dosimetric data required by the American Association of Physicists in Medicine Task Group 142 Report (AAPMTG 142 dated 2009) daily and monthly QA protocols. In addition, the quality assurance device is designed such that it may be used to acquire patient-specific QA data, including for patients being treated with intensity modulated radiation therapy (IMRT QA) and volume modulated arc therapy (VMAT) as well as any other modulated, or non-modulated treatment modality.

SUMMARY

In accordance with the purposes and benefits described herein, a new and improved apparatus is provided for assuring proper alignment and operation of a medical accelerator. That apparatus comprises a base and a translation stage supported on the base. The translation stage includes (a) a cradle, (b) a rotation adjustment assembly adapted for adjusting a rotational angle of the cradle with respect to the base, (c) a tilt adjustment assembly adapted for adjusting a tilt angle at which the cradle is positioned with respect to the base and (d) a position sensor adapted to provide accurate measurements of a current position of the cradle during cradle position adjustment.

In one or more of the many possible embodiments of the apparatus, the cradle has a plurality of lift points. The tilt adjustment assembly may include a stepper motor mounted at each lift point of the cradle. Each stepper motor may include a height adjustment screw.

In one or more of the many possible embodiments of the apparatus, the rotation adjustment assembly includes an annular support gear, a drive pinion and a stepper motor adapted so that the stepper motor drives the pinion which in turn drives the annular support gear to rotate the cradle around an axis A. The annular support gear may include a plurality of receivers corresponding in number and location to the plurality of lift points of the cradle. Each height adjustment screw may include a support tip and each support tip may be received in one of the receivers in the annular support gear below the lift points of the cradle.

The base may include a guide track for the annular support gear. That guide track may be a raised circular rail on an upper face of the base. The pinion may rotate on a stub shaft projecting from the upper face of the base.

In one or more of the many possible embodiments of the apparatus, the apparatus includes a controller configured to control operation of the stepper motors of the tilt adjustment assembly and the rotation adjustment assembly. That controller may be further configured to receive data from the position sensor respecting the current position of the cradle.

Still further, the apparatus may include a quality assurance device supported on the cradle. The quality assurance device may include cross hair alignment indicia and the controller may be further configured to be responsive to optical feedback respecting a current position of the cross hair alignment indicia on the quality assurance device with a reference frame provided by room lasers when adjusting the position and angular orientation of the quality assurance device and acquiring quality assurance measurements on a medical linear accelerator.

In accordance with yet another aspect, an apparatus adapted for automated device alignment for radiation therapy quality assurance, comprises: (a) a base, (b) a rotation adjustment assembly supported on the base, (c) a tilt adjustment assembly supported on the rotation adjustment assembly, (d) a quality assurance device supported on a cradle of the tilt adjustment assembly, (e) a position sensor adapted to provide accurate measurements of a current position of the cradle during cradle position adjustment, and (f) a controller configured to control operation of the rotation adjustment assembly and the tilt adjustment assembly and receive data from the position sensor respecting the current position of the cradle.

In one or more of the many possible embodiments of the apparatus, the quality assurance device includes cross hair alignment indicia and the controller is further configured to be responsive to optical feedback respecting a current position of the cross hair alignment indicia on the quality assurance device with a reference frame provided by room lasers when adjusting the position and angular orientation of the quality assurance device to acquire quality assurance measurements on a medical linear accelerator.

In one or more of the many possible embodiments of the apparatus, the cradle has a plurality of lift points, the tilt adjustment assembly includes a stepper motor mounted at each lift point of the cradle and each stepper motor drives a height adjustment screw. The rotation adjustment assembly may include an annular support gear, a drive pinion and a stepper motor adapted so that the stepper motor drives the pinion which in turn drives the annular support gear to rotate the cradle around an axis A.

In accordance with yet an additional aspect, the annular support gear includes a plurality of receivers corresponding in number and location to the plurality of lift points of the cradle and each height adjustment screw includes a support tip and each support tip is received in one of the receivers in the annular support gear below the lift points of the cradle. The base may include a guide track for the annular support gear. That guide track may be a continuous, circular rib on or projecting from an upper face of the base. The pinion may rotate on a stub shaft projecting from the upper face of the base. Further, the controller may be configured to control operation of the stepper motors of the tilt adjustment assembly and the rotation adjustment assembly.

In the following description, there are shown and described several preferred embodiments of the apparatus adapted for automated device alignment in radiation therapy quality assurance. As it should be realized, the apparatus is capable of other, different embodiments and its several details are capable of modification in various, obvious aspects all without departing from the apparatus as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the apparatus adapted for automated device alignment in radiation therapy quality assurance and together with the description serve to explain certain principles thereof.

FIGS. 11A-11C are a series of views illustrating how the cradle apparatus may be used to align and register the crosshair alignment indicia of the quality assurance device with the room laser generated reference frame to allow for the acquisition of accurate quality assurance measurements.

Reference will now be made in detail to the present preferred embodiments of the apparatus, examples of which are illustrated in the accompanying drawing figures.

DETAILED DESCRIPTION

Figure 1:
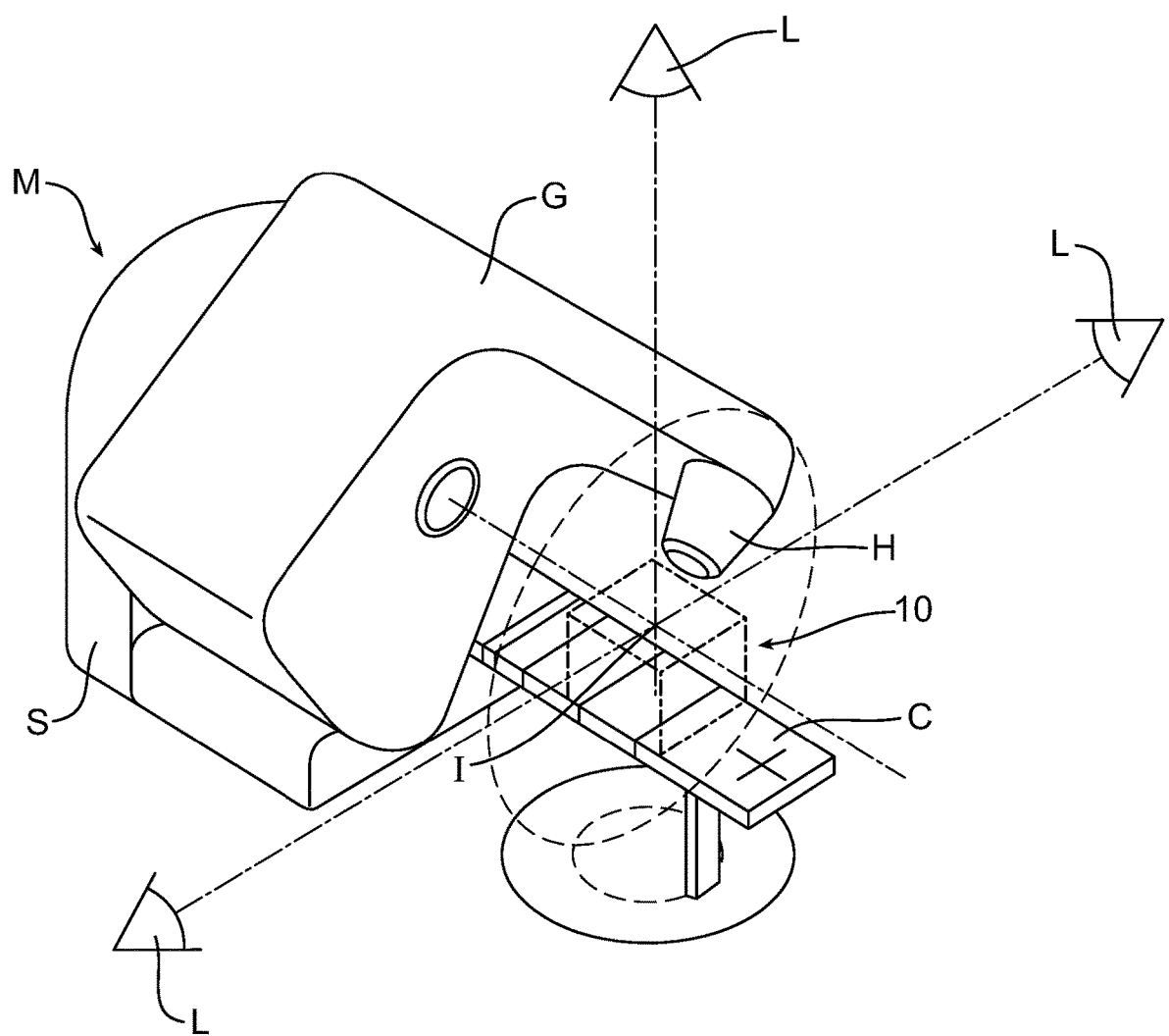
FIG. 1 is a perspective view of a medical accelerator that illustrates the quality assurance device positioned on the treatment couch, at the intersection of the room lasers, adjacent the gantry of the medical accelerator.

Reference is now made to FIG. 1 illustrating the new and improved quality assurance device 10 and a medical accelerator M. As illustrated, the medical accelerator M includes a gantry G supported for rotation with respect to a stand S. A treatment head H carried on the gantry G directs radiation toward a target located at the isocentre I. Room lasers L function to identify the isocentre I. As illustrated in FIG. 1, the quality assurance device 10 has been positioned on the treatment couch C of the medical accelerator M at the isocentre I using the room lasers L as a guide.

Figure 2:
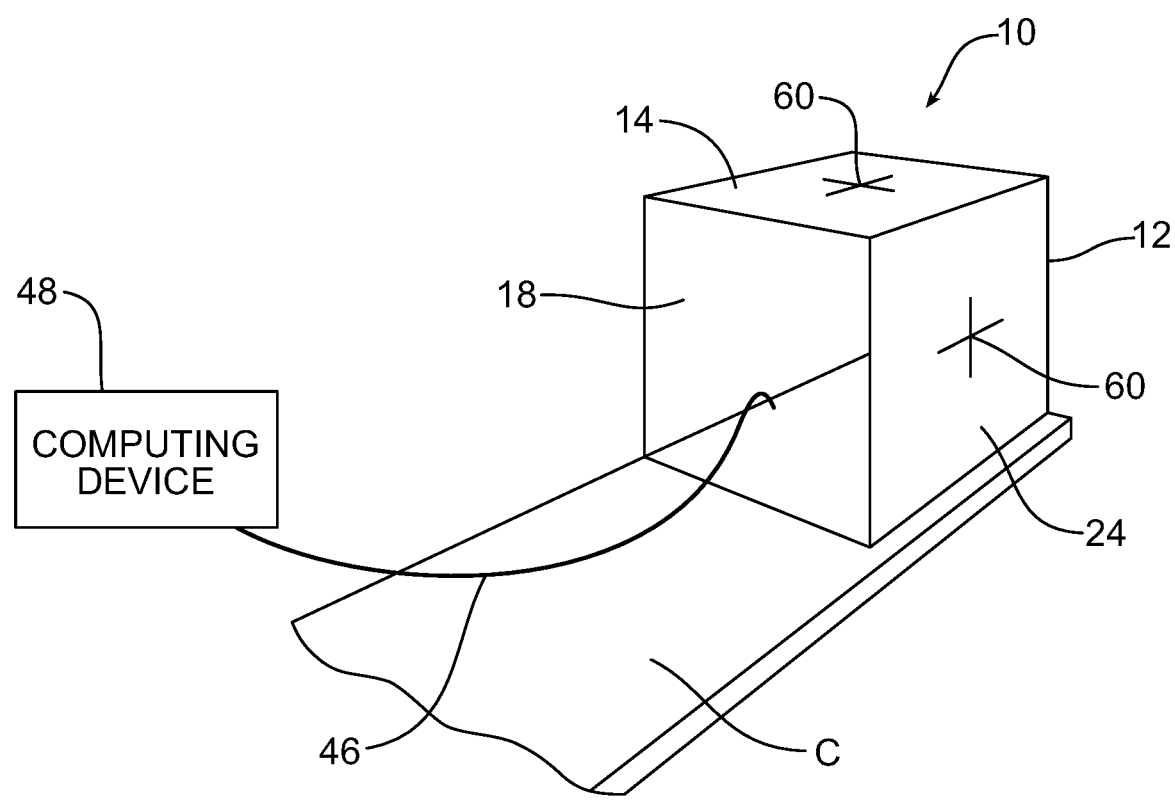
FIG. 2 is a detailed perspective view illustrating a quality assurance device including the housing and the electrical/communications cable protruding from the housing and connecting the electronic components contained in the housing to the computing device that controls the operation of the quality assurance device.
Figure 3:
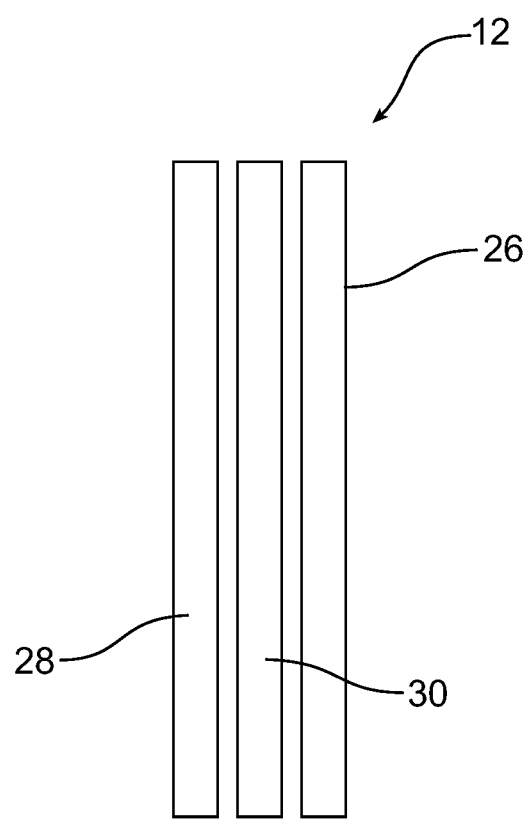
FIG. 3 is a schematic illustration of the construction of the housing including the inner scintillation layer, the outer switchable material layer and the intermediate mechanical layer for structural integrity.

Reference is now made to FIGS. 2-6 which when considered together illustrate the structure of the quality assurance device 10. As shown, the quality assurance device 10 comprises a housing 12. In the illustrated embodiment, the housing 12 has the overall shape of a cube including six sides 14, 16, 18, 20, 22 and 24. When positioned on the treatment couch C to perform quality assurance testing of the medical accelerator M, the side 14 faces up, the side 16 faces down toward the treatment couch and the side 22 is oriented toward the gantry G. As illustrated in FIG. 3, each side 14, 16, 18, 20, 22, 24 includes an inner scintillation or radioluminescent layer 26, an outer layer 28 made from a semitransparent or switchable material and an intermediate structural layer 30 to provide strength and rigidity.

More particularly, the inner radioluminescent layer 26 is adapted to provide a visual indication when contacted with invisible radiation generate by the medical accelerator M. The outer layer 28 may be made from a semitransparent material. In one or more of the many possible embodiments of the quality assurance device 10, the outer layer 28 is made from a switchable material of a type known in the art having a first state wherein visible light passes through the switchable material and a second state wherein visible light is at least partially and in some embodiments totally obstructed from passing through the switchable material.

Figure 4:
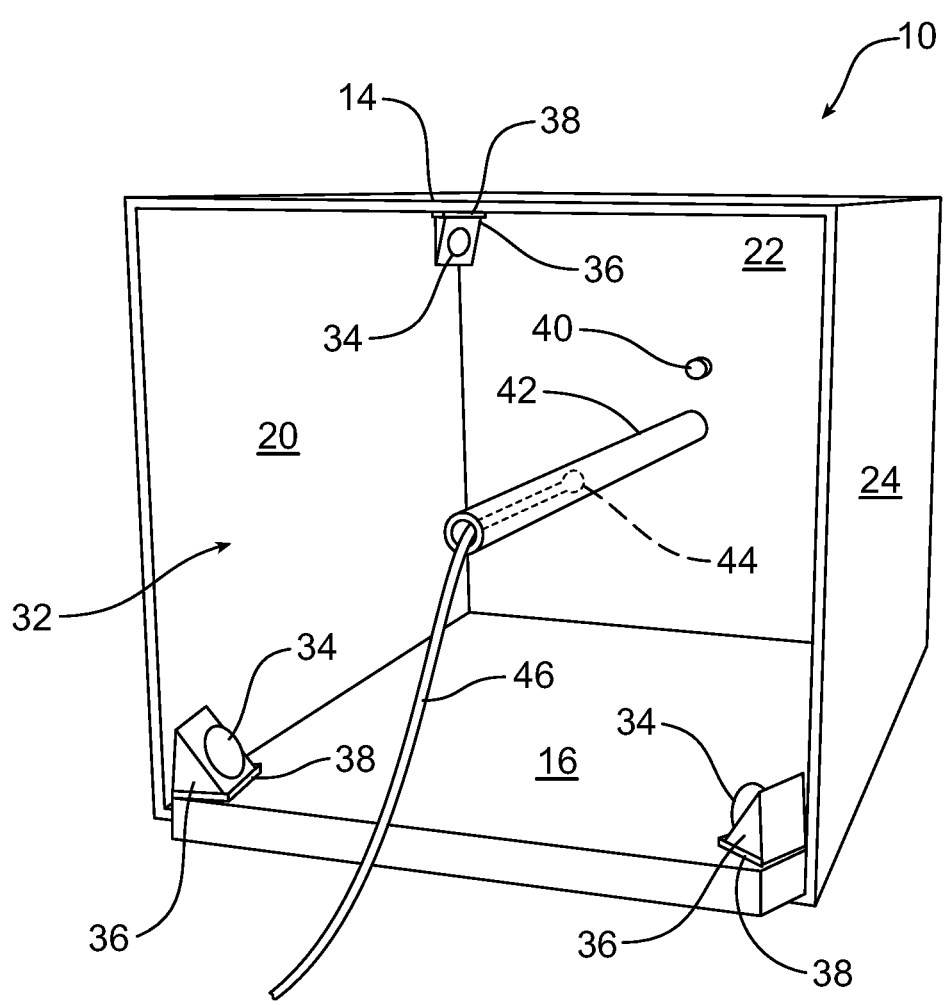
FIG. 4 is a perspective view of the quality assurance device with a sidewall of the housing removed to illustrate three cameras and an integrated radiation detector held in inserts within the housing.

FIG. 4 illustrates the quality assurance device 10 with a side 18 removed to illustrate the interior 32 of the quality assurance device 10. In the illustrated embodiment, three cameras 34 are held in inserts 36 that may be removably mounted in receivers 38 at three corners of the housing 12. As will be described in greater detail below, these cameras 34 are adapted to image the inner radioluminescent layer 26 of the housing 12 including the visual indication that is produced when the inner radioluminescent layer 26 is contacted with invisible radiation generated by the medical accelerator M.

As further illustrated in FIG. 4, an optional calibrated light source 40 is located within the housing 12. In the illustrated embodiment that calibrated light source 40 is illustrated positioned on the inner surface of the side 22.

As further illustrated in FIG. 4, a removable support tube 42 is also mounted to the side 22. A radiation detector 44 is located within the housing carried by or embedded in the support tube 42. An electrical/communications cable 46 protrudes through the side 18 (see also FIG. 2) and functions to connect the various electronic devices within the housing 12 including the cameras 34, calibrated light source 40 and radiation detector 44 with a computing device 48 located outside of the housing 12. That computing device 48 may comprise one or more processors, one or more memories and one or more network interfaces all in communication with each other over a communication bus. In one or more embodiments, the computing device 48 may comprise a dedicated microprocessor or an electronic control unit (ECU) operating in accordance with instructions from appropriate control software.

The computing device 48 may be adapted or configured to (a) convert light intensity detected by at least one camera 34 to radiation dose delivered by the medical accelerator M, (b) convert light intensity detected by the at least one camera 34 to radiation fluence of the medical accelerator, (c) convert spatial location of the visual indication on the inner radioluminescent layer 26 to a coordinate system that is defined relative to the medical accelerator and (d) compare locations of the radiation and radiation boundaries to the locations indicated by sources of visible light including, for example, the room lasers L, any medical accelerator light field and any medical accelerator crosshairs associated with the medical accelerator M being tested for quality assurance utilizing the quality assurance device 10. The computing device 48 may also be configured to receive signals from either or both of the calibrated light source and the removable radiation detector and acquire or interpret data coming from those components.

Figure 5:
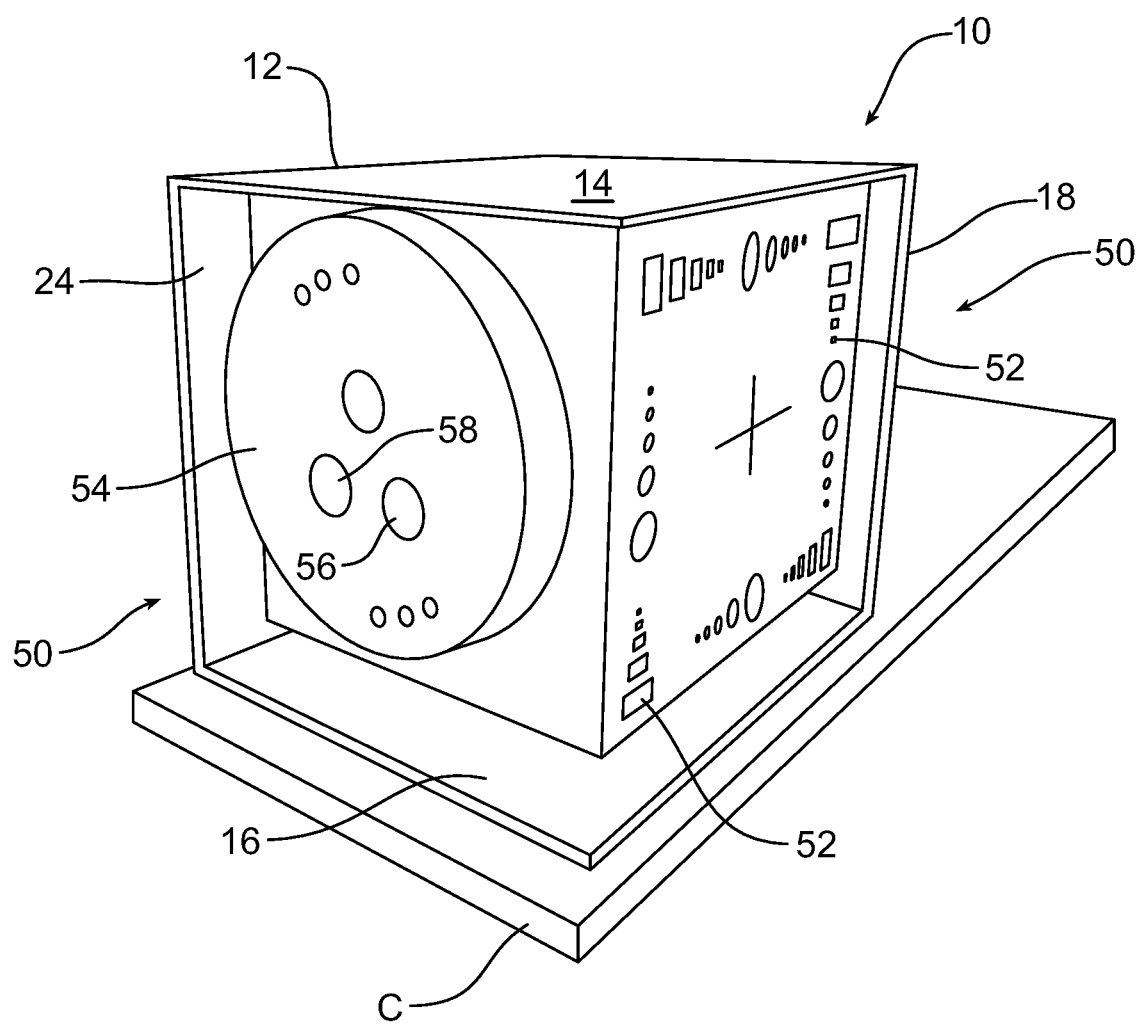
FIG. 5 is a perspective view of the quality assurance device illustrating a CT image quality phantom on a superior side of the housing located closest to the gantry of the medical accelerator and a first group of imaging test objects on an adjacent side of the housing.
Figure 6:
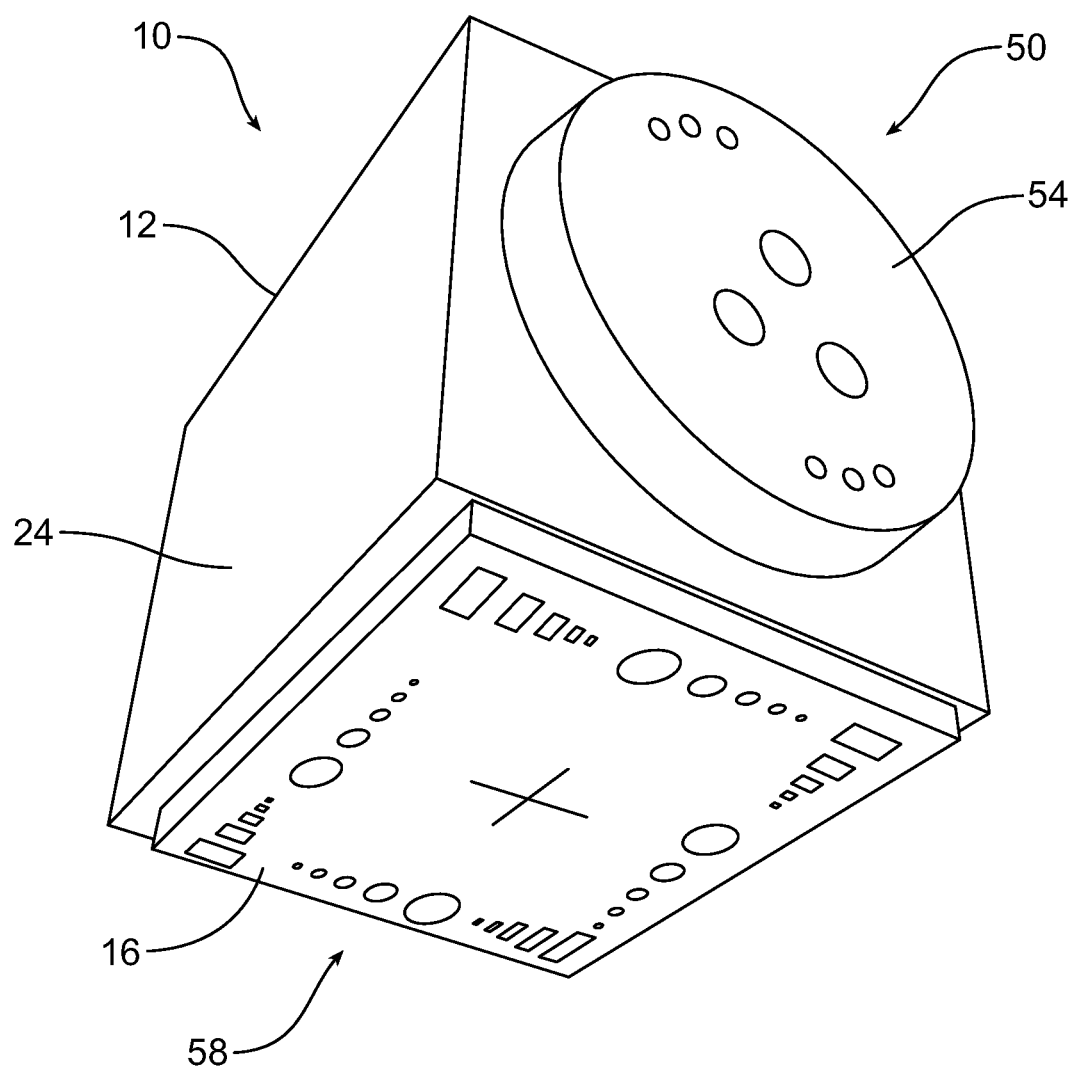
FIG. 6 is a perspective view of the bottom of the quality assurance device with the lower wall removed and illustrating the second group of imaging test objects adjacent the lower surface of the housing.

As illustrated in FIGS. 5 and 6, the quality assurance device 10 further includes at least one imaging test object 50 carried on the housing 12. That at least one imaging test object 50 may include a first group 52 positioned along a side, such as the side 20 of the housing 12. The first group of imaging test objects 52 are adapted to evaluate diagnostic, k V image quality including spatial resolution, contrast resolution and geometric integrity. As further illustrated in FIG. 5, the at least one imaging test object 50 may also include a CT image quality phantom 54 on the side 22 which is oriented toward and closest to the accelerator gantry G of the medical accelerator M when the quality assurance device 10 is positioned for testing. More particularly, the CT image quality phantom 54 may include a radioluminescent phosphor 56 on one side visible to at least one of the cameras 34 and a radiation dose detector 58.

As illustrated in FIG. 6, the at least one imaging test object 50 may also include a second group of imaging test objects 58 positioned on the side 16 which faces down toward the treatment couch C when the quality assurance device 10 is positioned for testing. The second group of imaging test objects 58 is adapted to evaluate mega-voltage (MV) image quality of an electronic portal imaging device (EPID) of the medical accelerator M including spatial resolution, contrast resolution and geometric integrity.

The quality assurance device 10 illustrated in FIGS. 1-6 is useful in a method of quality assurance for a medical accelerator M. That method includes the step of positioning the quality assurance device 10 on the treatment couch C of the medical accelerator M. More particularly, as illustrated in FIGS. 1 and 2, the quality assurance device 10 is positioned on the treatment couch C with the assistance of the room lasers L and crosshair alignment indicia 60 provided on the exterior of one or more sides 14, 16, 18, 20, 22, 24 of the housing 12. This ensures that the quality assurance device 10 is properly positioned with respect to the isocentre I of the medical accelerator M. During the positioning of the quality assurance device 10 on the treatment couch C, the switchable material on the outer layer 28 of the housing 12 may be switched into a first state wherein visible light passes through the switchable material. This further aids in the positioning of the device 10. Note also that the quality assurance device is positioned with the side 14 oriented upward, the side 16 oriented downward and the side 22 oriented toward the gantry G.

Once the quality assurance device 10 has been properly positioned on the treatment couch C, the method includes switching the switchable material into a second state wherein visible light is at least partially obstructed from passing through the switchable material. This either diminishes or eliminates ambient room lighting from passing through the housing 12 into the interior 32 of the housing where such light can interfere with detection of the visual indication of the radiation that is produced or generated when the invisible radiation generated by the medical accelerator M impinges upon the inner radioluminescent layer 26 of the housing 12.

The method also includes the step of detecting the radiation delivered by the medical accelerator M to the quality assurance device 10. As noted, that radiation produces a visual indication on the inner layer 26 of the housing 12 of the quality assurance device 10. Toward this end, the method includes imaging that visual indication with the camera or cameras 34 located within the housing 12 of the quality assurance device 10. The image of that visual indication is then communicated through the electrical/communication cable 46 to the computing device 48 which has been adapted or configured to: (a) convert light intensity detected by the camera or cameras 34 to radiation dose, (b) convert light intensity detected by the at least one camera to radiation fluence, (c) convert spatial location of the visual indication on the inner radioluminescent layer 26 to a coordinate system as defined relative to the medical accelerator M and (d) compare locations of the radiation and radiation boundaries to the locations indicated by sources of visible light including the room lasers L, a medical accelerator light field and any medical accelerator crosshairs associated with the medical accelerator. In this way it is possible to properly calibrate and ensure optimization of function of the medical accelerator M in a simple and efficient manner. Still further, the method may also include the steps of receiving signals from either or both of the calibrated light source and the removable radiation detector and acquiring or interpreting data coming from those components.

A number of benefits and advantages are associated with the quality assurance device 10 as well as the method of quality assurance for a medical accelerator M. The positioning of the camera or cameras 34 within the housing 12 allows for a more compact quality assurance device 10 having a smaller form factor and also allows for the acquisition of more data with fewer cameras as well as for the acquisition of data without having to reposition the cameras during operation of the medical accelerator M and rotation of the gantry G.

The use of the switchable material or switchable glass for the outer layer 28 of the housing 12 allows for the exclusion of ambient room light from the interior 32 of the housing 12. This allows the camera or cameras 34 to detect smaller changes in the visual indications of the radiation and thus in radiation dose and, thereby, allows for the collection of higher quality data.

At the same time, when the switchable material of the outer layer 28 is in a first state during positioning of the quality assurance device 10 on the treatment couch C, visible room light including positioning markers from the room lasers L, any medical accelerator light field and medical accelerator crosshairs allow the cameras to uniquely record the positioning of the quality assurance device 10 relative to these external positioning features.

By integrating the imaging test objects 50, including the first group of test objects 52, the CT image quality phantom 54 and the second group of test objects 58 into the housing 12 of the quality assurance device 10 all TG 142 monthly compliance data may be acquired utilizing the quality assurance device 10 with minimal operator intervention.

The placement or positioning of the first group of imaging test objects 52 on the side 20 of the housing 12 and the second group of imaging test objects 58 on the lower side 16 of the housing 12 means that the gantry G on the majority of "conventional" medical accelerators M does not need to be rotated for the kV and MV image tests. This saves trips in and out of the treatment vault and thus time for data collection. The switchable material/switchable glass feature of the outer layer 28 of the housing 12 enables ambient room light to be excluded without the operator having to enter the room and place or remove a cover and thus also saves time and contributes to the efficiency in using the quality assurance device 10.

The quality assurance device 10 and the related method described herein allow the acquisition of comprehensive TG 142 data in 30 minutes or less with a minimum of operator intervention. The ease of use and automation provided by the quality assurance device 10 and related method is such that the quality assurance procedure can be completed by technicians as well as qualified medical physicists.

Data from the integrated radiation detector 44 can be electronically read by the computing device 48 and uploaded to a centralized data repository. The data readings can be compared to other clinics' data so that inter-institutional comparisons can be made. In doing so, individual clinics will know if the calibration of their medical accelerator is within a normal range. These readings can be collected and analyzed automatically on a daily basis so that deviations are revealed in a timely way. Further, the integrated radiation detector 44 may be housed in a removable insert (i.e. removable support tube 42) that can be shipped to a centralized calibration facility and then repositioned in the device 10 with a high degree of reproducibility. Similarly, the camera or cameras 34 are embedded in the rigid inserts 36 that can be removed and replaced as necessary. In this manner the cameras 34 may be regarded as disposable device components and can be readily replaced. This mitigates concerns regarding any potential radiation damage to the performance of the cameras over time.

The calibrated light source 40 within the housing 12 functions to ensure the stability of the light intensity observed by the camera or cameras 34. This is done by comparing the measured light intensity to the known/calibration intensity so that any variations in the imaging system response can be corrected.

As a further benefit and advantage, the quality assurance device 10 is designed such that the light/radiation detecting camera or cameras 34 are stationary during all data collection. Other systems having cameras that are attached to the medical accelerator or that must be synchronously rotated with the accelerator gantry do not allow for the isolation of variables during data analysis as provided by the quality assurance device 10.

Advantageously, the CT image quality phantom 54 is coated on one side with a radioluminescent phosphor 56 that is visible by one or more of the cameras 34 within the housing 12. The intensity of light coming from the phosphor changes with the intensity of the radiation it receives. In this way, the CT image quality phantom 54 is able to acquire a full, two-dimensional picture of the radiation distribution, commonly referred to as "percent depth dose." The CT image quality phantom 54 also advantageously allows for measurement of electron beam characteristics. Further, the CT imaging phantom 54 may also have a diode, diodes and ionization chamber or ionization chambers or other detectors embedded within in order to assess the absolute radiation dose delivered to the device 10.

Reference is now made to FIGS. 7, 8, 9, 10A, 10B and 11A-11C which illustrate the structure and operation of a cradle apparatus 100 adapted to hold and adjust the position and angular orientation of the quality assurance device 10 for acquiring accurate quality assurance measurements on medical linear accelerators M as used for radiation therapy of cancer patients.

Figure 7:
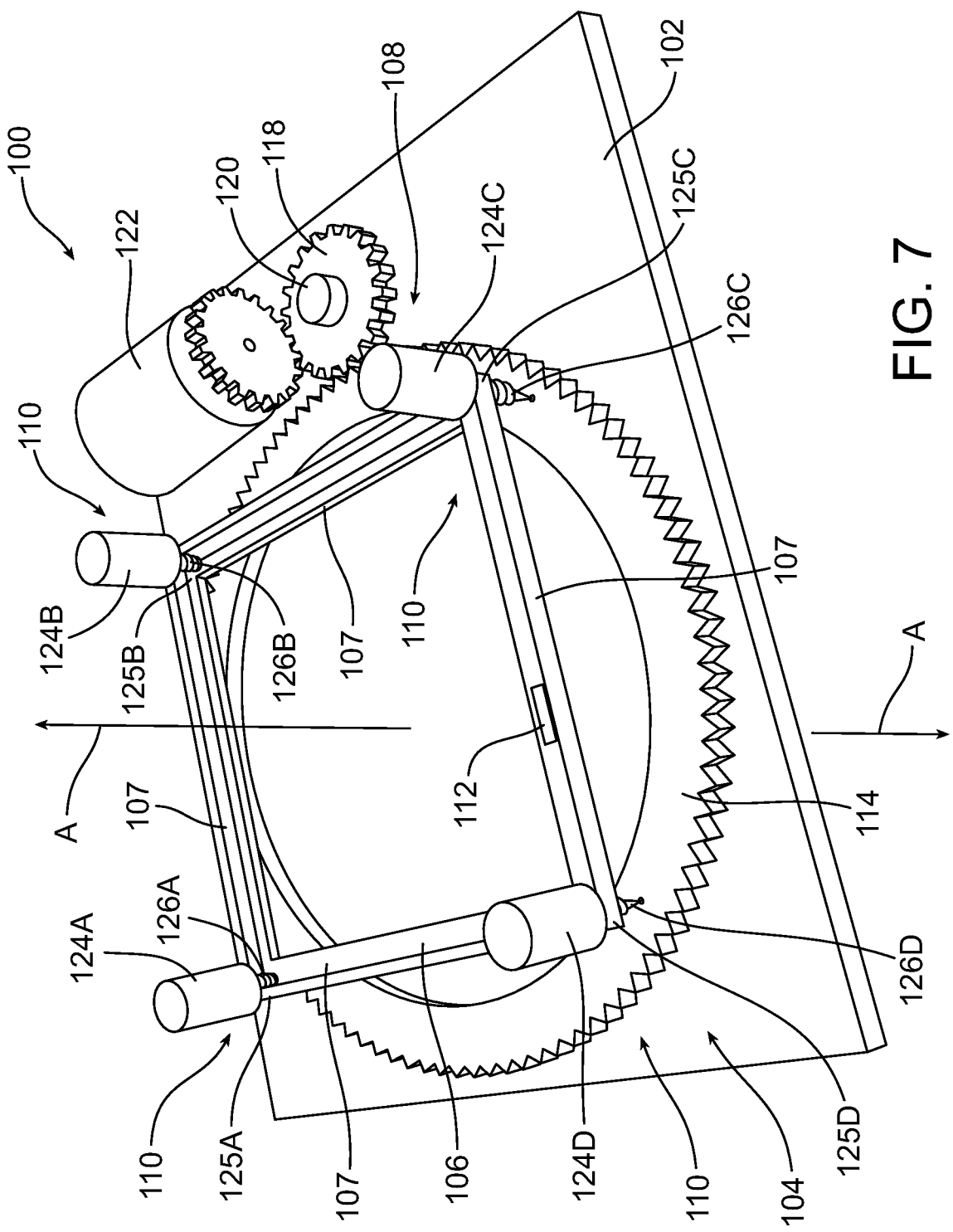
FIG. 7 is a perspective view of a cradle assembly adapted for holding and adjusting the position and angular orientation of a quality assurance device for acquiring accurate quality assurance measurements on medical linear accelerators.
Figure 8:
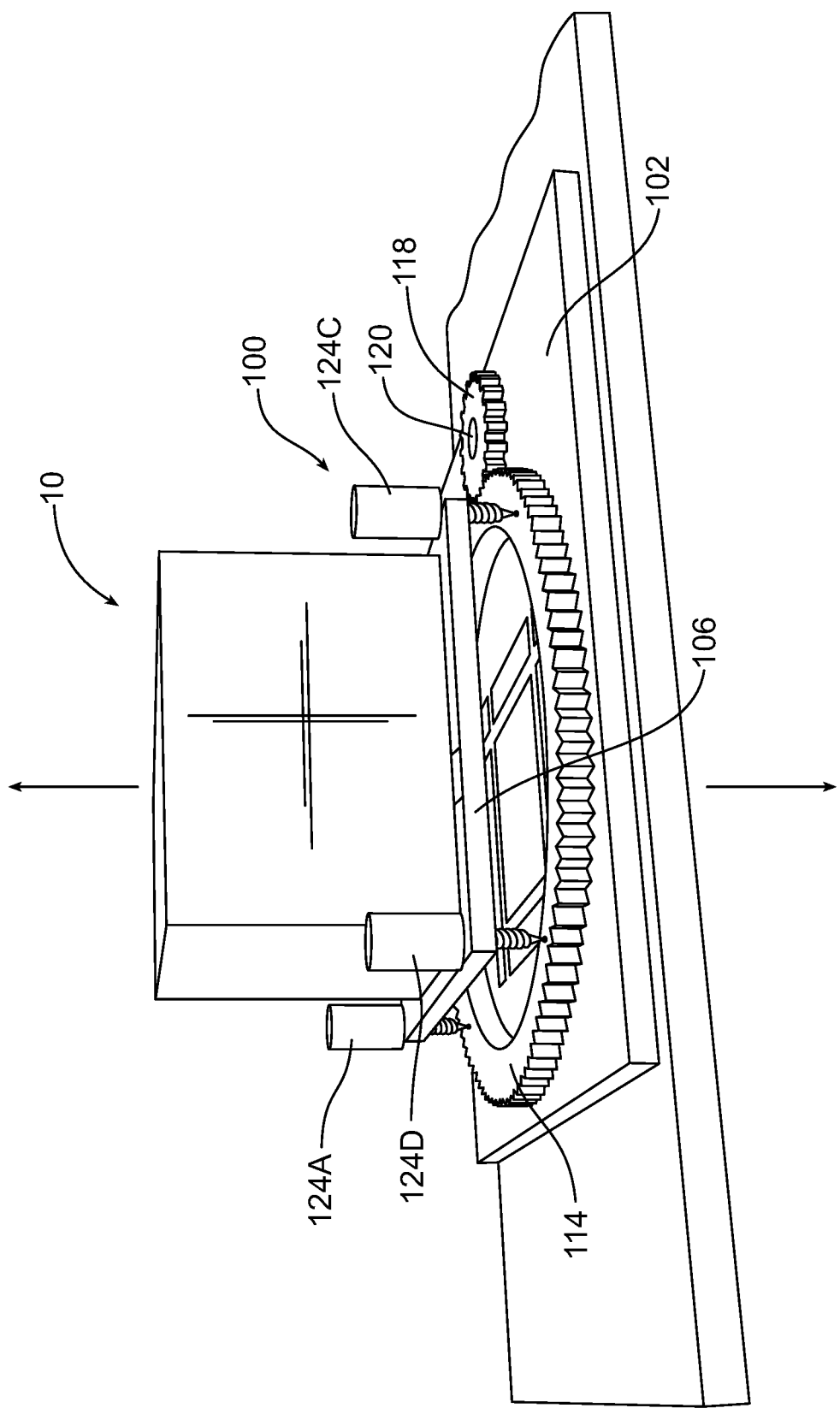
FIG. 8 is a perspective view of the cradle apparatus of FIG. 7 holding the quality assurance device of FIG. 2.

The cradle apparatus 100 includes a base 102 that supports a translation stage generally designated by reference numeral 104 (See FIGS. 7 and 8). The translation stage 104 includes (a) a cradle 106, adapted for receiving and holding the quality assurance device 10, (b) a rotation adjustment assembly 108, adapted for adjusting the rotational orientation of the cradle and quality assurance device with respect to the base 102, (c) an angular adjustment assembly 110 adapted to adjust the angle at which the cradle and quality assurance device are positioned with respect to the rotation adjustment assembly and the base and (d) a position sensor in the form of a precision inclinometer 112 to provide accurate measurements of the angular position of the cradle and quality assurance device during and after position adjustment.

In the illustrated embodiment, the cradle 106 includes four sides 107 that are sized to hold the quality assurance device as illustrated in FIG. 8. The rotation adjustment assembly 108 includes: (a) an annular support gear 114 that rotates along a track 116, such as a continuous, circular raised rail, on the upper face of the base 102 that is received in a cooperating channel 117 in the bottom of the annular support gear, (b) a drive pinion 118 that rotates on a stub shaft 120 projecting from the upper face of the base and (c) a stepper drive motor 122 that engages and drives the pinion which, in turn engages and drives the annular support gear. As should be appreciated, the drive motor 122 of the rotation adjustment assembly 108 rotates the cradle 106 and the quality assurance device 10 held thereon about the axis A (running through the center point of the annular support gear) into any desired rotation position.

The angular adjustment assembly 110 is carried on the annular support gear 114. More specifically, the angular adjustment assembly 110 includes four stepper motors 124A, 124B, 124C and 124D mounted on the cradle 106. More specifically, one stepper motor 124A, 124B, 124C, 124D is mounted at each lift point 125A, 125B, 125C, 125D of the cradle 106 (which corresponds to the corners of the cradle and the corners of the quality assurance device housing 12 when the quality assurance device 10 is held on the cradle in the illustrated embodiment). Each stepper motor 124A, 124B, 124C, 124D is connected, respectively, to cooperating height adjustment screws 126A, 126B, 126C and 126D. Each height adjustment screw 126A, 126B, 126C and 126D has a point or support tip 128 that nests in one receiver 130 formed in the annular support gear 114 that are aligned with respective lift points 125A, 125B, 125C and 125D of the cradle 106 (see FIG. 9 for detailed view). This arrangement serves to hold the cradle 106 in place on the annular support gear 114 while allowing the screws 126A-126D to turn freely in the receivers 130 to provide for height adjustment at each lift point 125A-125D of the cradle. The stepper motors 122 and 124A-124D allow for precise movements when rotating and tilting the cradle 106 and the quality assurance device 10 held therein.

In one or more of the many possible embodiments of the cradle apparatus 100, a hand-held controller 140 (See FIG. 10A) may be used to manually operate the individual stepper motors 122 and 124A-124D in order to align the crosshair alignment indicia 60 of the quality assurance device 10 with the reference frame RF provided by the room lasers L. See, for example, the toggle switch 142 that is connected to the stepper drive motor 122 to rotate the cradle 106 and the quality assurance device 10 in a clockwise or counter clockwise direction about the axis A, and the respective toggle switches 144A-144D that are connected to the respective stepper motors 124A-124D to raise and lower the respective lift points 125A-125D of the cradle and the quality assurance device.

Figure 9:
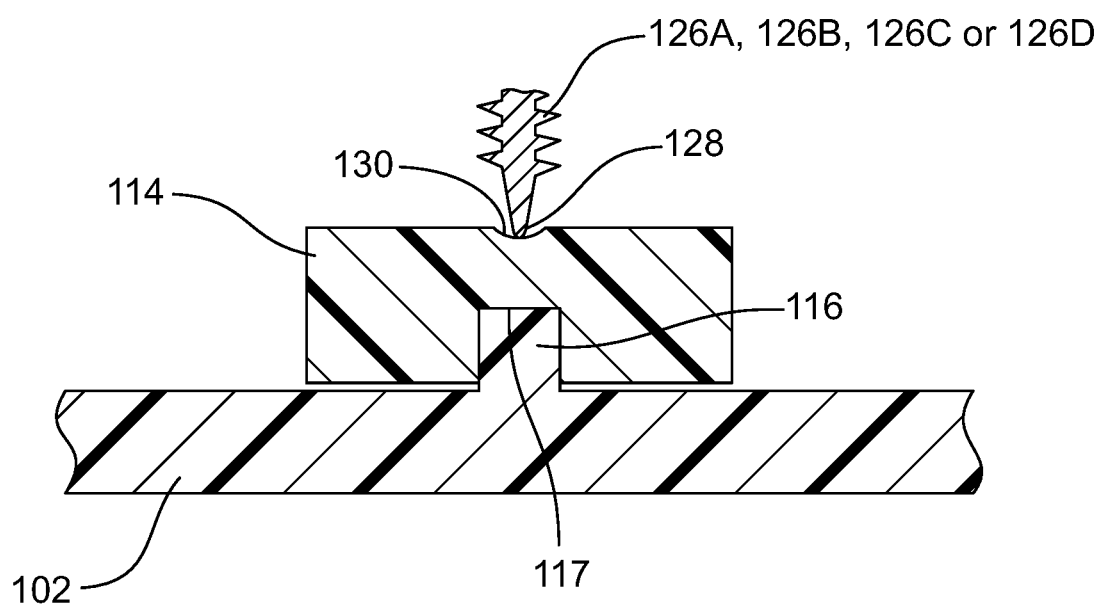
FIG. 9 is a detailed cross-sectional view of the base, the guide track for the annular support gear, the annular support gear and one height adjustment screw.
Figure 10A:
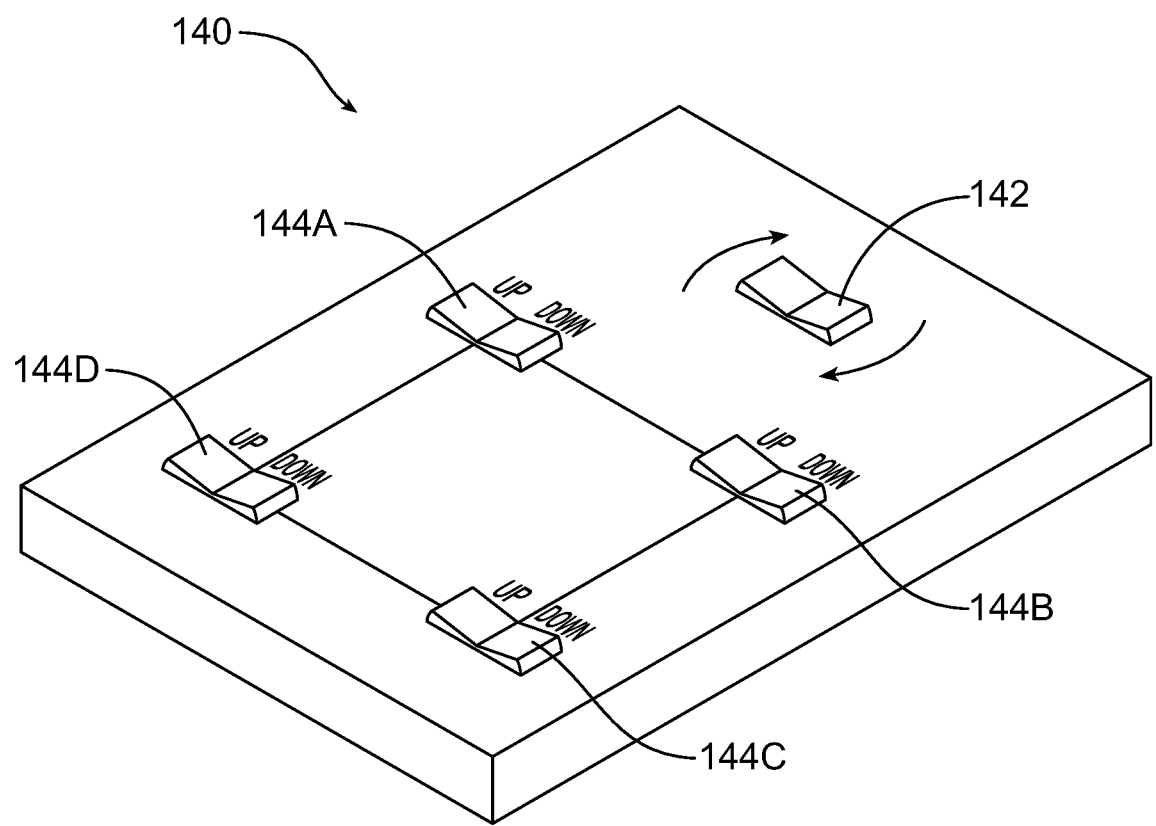
FIG. 10A is a detailed perspective view of a hand held controller for the cradle apparatus.
Figure 10B:
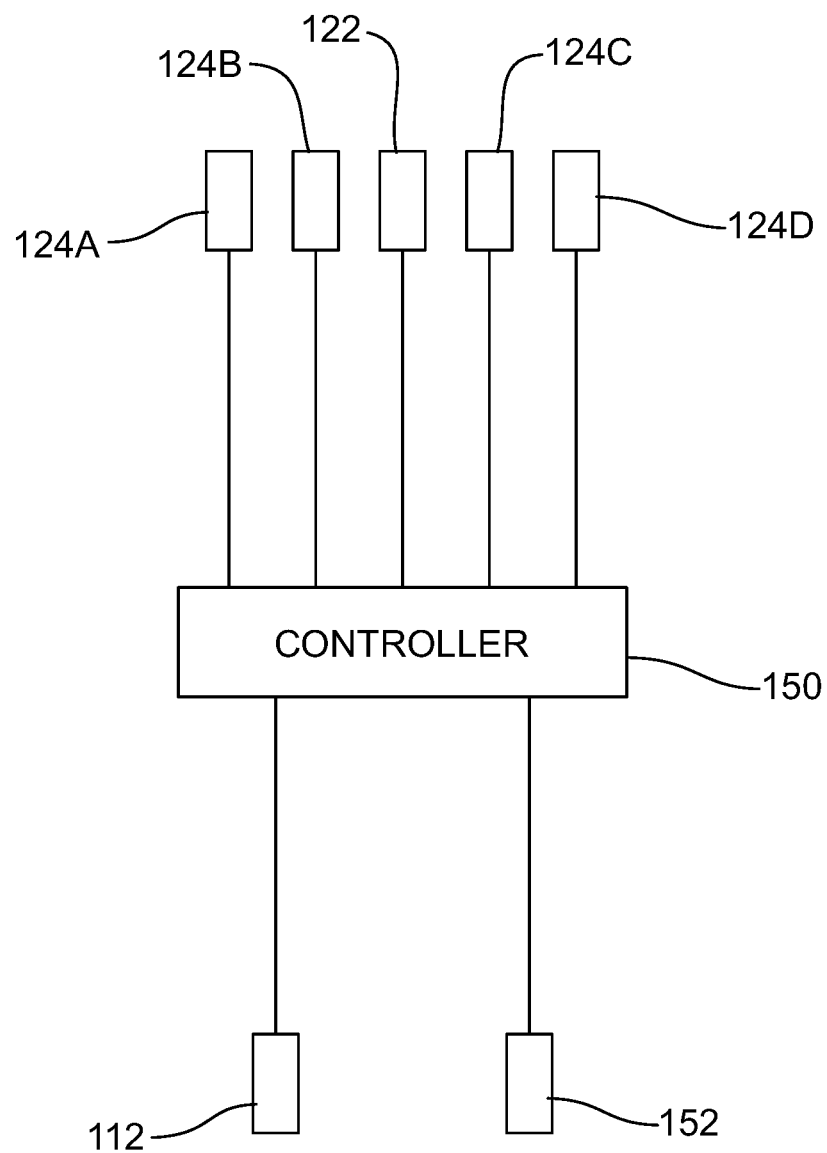
FIG. 10B is a schematic view of an automatic control system for the cradle apparatus.

As illustrated in FIG. 10B, in one or more of the many possible embodiments of the cradle apparatus 100, the rotational and angular position of the cradle 106 and the quality assurance device 10 held therein may be automatically adjusted. More particularly, as illustrated in FIG. 9, the cradle apparatus 100 may include a controller 150 configured or adapted for automatically moving the position of the cradle 106 and the quality assurance device 10 held thereon into proper position for acquiring accurate quality assurance measurements on a medical linear accelerator M. The controller 150 may, for example, take the form of a dedicated microprocessor or an electronic control unit (ECU) operating in accordance with instructions from appropriate control software.

The controller 150 is connected to and controls operation of (a) the stepper drive motor 122 to control the rotational orientation of the cradle 106 and the quality assurance device 10 held thereon and (b) the stepper motors 124A-124D at the four lift points 125A-125D of the cradle 106 to control the tilt or angular orientation of the cradle and the quality assurance device relative to the rotation axis A. The controller 150 is also connected to the precision inclinometer 112 to receive data related to the movement and position of the cradle 106 and the quality assurance device 10 at all times. In such an embodiment, the controller 150 is also responsive to optical feedback respecting the position of the crosshair alignment indicia 60 of the quality assurance device 10 with the reference frame RF provided by the room lasers L (see also FIGS. 11A-11C) when adjusting the position and angular orientation of the quality assurance device 10 for acquiring accurate quality assurance measurements on the medical linear accelerator M. The laser light location of the reference frame RF with respect to the crosshair alignment indicia 60 may be monitored by any appropriate monitoring device 152 for such a purpose including a camera, a photodiode or a like device adapted to provide position feedback data to the controller.

Figure 11B:
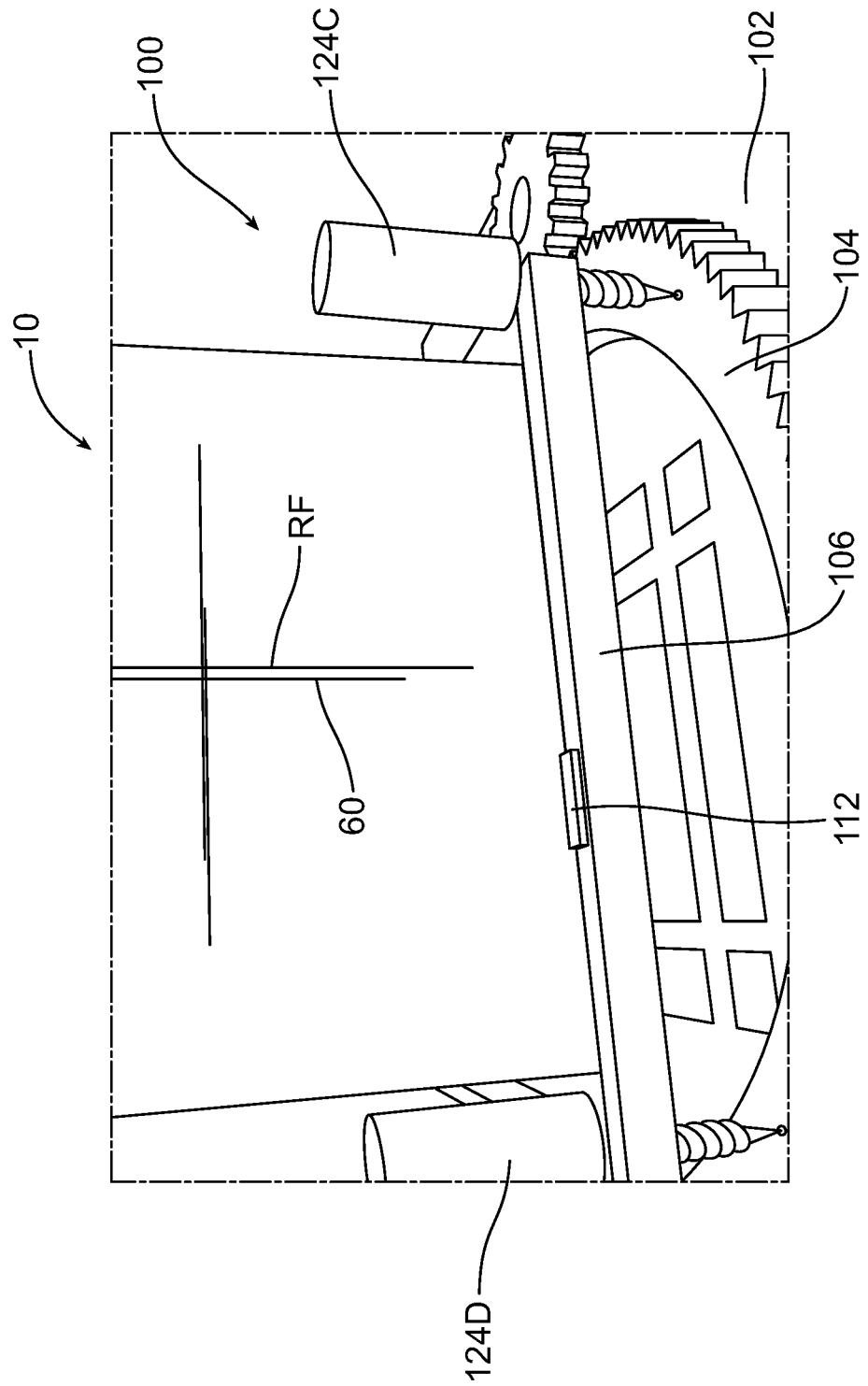

FIGS. 11A-11C illustrate how the position of the cradle 106 and the quality assurance device 10 held thereon may be adjusted in order to bring the quality assurance device into proper alignment and registration with an external reference frame RF, such as may be generated by the room lasers L of the medical accelerator coordinate system.

First, the rotational position of the cradle 106 and the quality assurance device 10 held thereon may be initially adjusted via the rotation adjustment assembly 108 and the drive motor 122 to bring the quality assurance device into coarse alignment with the reference frame RF. Note and compare FIG. 11A with FIG. 11B. Next, the angular position of the cradle 106 and the quality assurance device held thereon is adjusted via the angular adjustment assembly 110 and the stepper motors 124A-124D to bring the quality assurance device, first into finer alignment and then into full alignment or registration (see FIG. 11C) with the room lasers L. This may be done manually using the hand held controller 140 illustrated in FIG. 10A or automatically by the controller 150 illustrated in FIG. 10B. In order to provide for the automatic adjustment noted above, the controller 150 is configured to be responsive to optical feedback from the monitoring device 152 respecting a current position of the cross hair alignment indicia 60 on the quality assurance device 10 with the reference frame RF provided by room lasers L.

This document may be said to relate to the following items.
1. An apparatus, comprising:
    a base;
    a translation stage supported on the base, the translation stage including (a) a cradle, (b) a rotation adjustment assembly adapted for adjusting a rotational angle of the cradle with respect to the base, and (c) a tilt adjustment assembly adapted for adjusting a tilt angle at which the cradle is positioned with respect to the base.
2. The apparatus of item 1, further including a position sensor adapted to provide accurate measurements of a current position of the cradle during cradle position adjustment.
3. The apparatus of item 2, wherein the cradle has a plurality of lift points.
4. The apparatus of item 3, wherein the tilt adjustment assembly includes a stepper motor mounted at each lift point of the cradle.
5. The apparatus of item 4, wherein each stepper motor drives a height adjustment screw.
6. The apparatus of item 5, wherein the rotation adjustment assembly includes an annular support gear, a drive pinion and a stepper motor adapted so that the stepper motor drives the pinion which in turn drives the annular support gear to rotate the cradle around an axis A.
7. The apparatus of item 6, wherein the annular support gear includes a plurality of receivers corresponding in number and location to the plurality of lift points of the cradle.
8. The apparatus of item 7, wherein each height adjustment screw includes a support tip and each support tip is received in one of the receivers in the annular support gear below the lift points of the cradle.
9. The apparatus of item 8, wherein the base includes a guide track for the annular support gear.
10. The apparatus of item 9, wherein the guide track is a circular rail on an upper face of the base and the pinion rotates on a stub shaft projecting from the upper face of the base.
11. The apparatus of any of items 4-10, further including a controller configured to control operation of the stepper motors of the tilt adjustment assembly and the rotation adjustment assembly.
12. The apparatus of item 11, wherein the controller is further configured to receive data from the position sensor respecting the current position of the cradle.
13. The apparatus of item 12, further including a quality assurance device supported on the cradle.
14. The apparatus of item 13, wherein the quality assurance device includes cross hair alignment indicia and the controller is further configured to be responsive to optical feedback respecting a current position of the cross hair alignment indicia on the quality assurance device with a reference frame provided by room lasers when adjusting the position and angular orientation of the quality assurance device when acquiring quality assurance measurements on a medical linear accelerator.

15. The apparatus of item 1, wherein the base includes a guide track for the annular support gear.

16. The apparatus of item 15, wherein the guide track is a circular rail on an upper face of the base and the pinion rotates on a stub shaft projecting from the upper face of the base.

17. An apparatus adapted for automated device alignment in radiation therapy quality assurance, comprising:
a base;
a rotation adjustment assembly supported on the base;
a tilt adjustment assembly supported on the rotation adjustment assembly;
a quality assurance device supported on a cradle of the tilt adjustment assembly;
a position sensor adapted to provide accurate measurements of a current position of the cradle during cradle position adjustment; and
a controller configured to receive data from the position sensor respecting the current position of the cradle and control operation of the rotation adjustment assembly and the tilt adjustment assembly.

18. The apparatus of item 17, wherein the quality assurance device includes cross hair alignment indicia and the controller is further configured to be responsive to optical feedback respecting a current position of the cross hair alignment indicia on the quality assurance device with a reference frame provided by room lasers when adjusting the position and angular orientation of the quality assurance device to acquire quality assurance measurements on a medical linear accelerator.

19. The apparatus of item 18, wherein the cradle has a plurality of lift points, the tilt adjustment assembly includes a stepper motor mounted at each lift point of the cradle and each stepper motor drives a height adjustment screw.

20. The apparatus of any of items 17-19, wherein the rotation adjustment assembly includes an annular support gear, a drive pinion and a stepper motor adapted so that the stepper motor drives the pinion which in turn drives the annular support gear to rotate the cradle around an axis A.

21. The apparatus of item 20, wherein the annular support gear includes a plurality of receivers corresponding in number and location to the plurality of lift points of the cradle and each height adjustment screw includes a support tip and each support tip is received in one of the receivers in the annular support gear below the lift points of the cradle.

22. The apparatus of item 21, wherein the base includes a guide track for the annular support gear, wherein the guide track is a circular rail on an upper face of the base and the pinion rotates on a stub shaft projecting from the upper face of the base.

23. The apparatus of item 22, wherein the controller is configured to control operation of the stepper motors of the tilt adjustment assembly and the rotation adjustment assembly.

24. The apparatus of item 17, wherein the base includes a guide track for the annular support gear, wherein the guide track is a circular rail on an upper face of the base and the pinion rotates on a stub shaft projecting from the upper face of the base.

25. The apparatus of item 20, wherein the controller is configured to control operation of the stepper motors of the tilt adjustment assembly and the rotation adjustment assembly.

Each of the following terms written in singular grammatical form: "a", "an", and "the", as used herein, means "at least one", or "one or more". Use of the phrase "One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

The phrase "consisting of", as used herein, is closed-ended and excludes any element, step, or ingredient not specifically mentioned. The phrase "consisting essentially of", as used herein, is a semi-closed term indicating that an item is limited to the components specified and those that do not materially affect the basic and novel characteristic(s) of what is specified.

Terms of approximation, such as the terms about, substantially, approximately, etc., as used herein, refers to +10% of the stated numerical value.

The foregoing has been presented for purposes of illustration and description. It is not intended to be exhaustive or to limit the embodiments to the precise form disclosed. Obvious modifications and variations are possible in light of the above teachings. For example, the above description references treatment room alignment lasers as providing physical landmarks (e.g. a reference frame RF) for the positioning of the quality assurance device 10. In contrast, some medical linear accelerators M produce a medical accelerator light field or a visible radiation pattern, such as collimator cross hairs, jaw positions or multileaf collimators that act as alignment landmarks and can also be measured with a monitoring device 152, such as a camera or photodiode or the like, to give feedback for proper positioning of the quality assurance device 10 on the cradle 106 of the apparatus 100. Similarly, drive devices other than stepper motors 122 and 124A-124D may be used. All such modifications and variations are within the scope of the appended claims when interpreted in accordance with the breadth to which they are fairly, legally and equitably entitled.

What is claimed:
1. An apparatus, comprising:
a base;
a translation stage supported on the base, the translation stage including (a) a cradle, (b) a rotation adjustment assembly adapted for adjusting a rotational angle of the cradle with respect to the base, and (c) a tilt adjustment assembly adapted for adjusting a tilt angle at which the cradle is positioned with respect to the base.

2. The apparatus of claim 1, further including a position sensor adapted to provide accurate measurements of a current position of the cradle during cradle position adjustment.

3. The apparatus of claim 2, wherein (a) the cradle has a plurality of corners, (b) the tilt adjustment assembly includes a stepper motor mounted at each corner of the cradle, and (c) each stepper motor drives a height adjustment screw.

4. The apparatus of claim 1, wherein the rotation adjustment assembly includes an annular support gear, a drive pinion and a stepper motor adapted so that the stepper motor drives the pinion which in turn drives the annular support gear to rotate the cradle around an axis A.

5. The apparatus of claim 4, wherein the annular support gear includes a plurality of receivers corresponding in number and location to the plurality of corners of the cradle.

6. The apparatus of claim 5, wherein each height adjustment screw includes a support tip and each support tip is received in one of the receivers in the annular support gear below the corners of the cradle.

7. The apparatus of claim 6, wherein the base includes a guide track for the annular support gear.

8. The apparatus of claim 7, wherein the guide track is a circular rail on an upper face of the base and the pinion rotates on a stub shaft projecting from the upper face of the base.

9. The apparatus of claim 4, further including a controller configured to control operation of the stepper motors of the tilt adjustment assembly and the rotation adjustment assembly.

10. The apparatus of claim 9, wherein the controller is further configured to receive data from the position sensor respecting the current position of the cradle.

11. The apparatus of claim 10, further including a quality assurance device supported on the cradle wherein the quality assurance device includes cross hair alignment indicia and the controller is further configured to be responsive to optical feedback respecting a current position of the cross hair alignment indicia on the quality assurance device with a reference frame provided by room lasers when adjusting the position and angular orientation of the quality assurance device when acquiring quality assurance measurements on a medical linear accelerator.

12. The apparatus of claim 4, wherein the base includes a guide track for the annular support gear.

13. The apparatus of claim 12, wherein the guide track is a circular rail on an upper face of the base and the pinion rotates on a stub shaft projecting from the upper face of the base.

14. An apparatus adapted for automated device alignment in radiation therapy quality assurance, comprising:
a base;
a rotation adjustment assembly supported on the base;
a tilt adjustment assembly supported on the rotation adjustment assembly;
a quality assurance device supported on a cradle of the tilt adjustment assembly;
a position sensor adapted to provide accurate measurements of a current position of the cradle during cradle position adjustment; and
a controller configured to receive data from the position sensor respecting the current position of the cradle and control operation of the rotation adjustment assembly and the tilt adjustment assembly.

15. The apparatus of claim 14, wherein the quality assurance device includes cross hair alignment indicia and the controller is further configured to be responsive to optical feedback respecting a current position of the cross hair alignment indicia on the quality assurance device with a reference frame provided by room lasers when adjusting the position and angular orientation of the quality assurance device to acquire quality assurance measurements on a medical linear accelerator.

16. The apparatus of claim 15, wherein the cradle has a plurality of corners, the tilt adjustment assembly includes a stepper motor mounted at each corner of the cradle and each stepper motor drives a height adjustment screw.

17. The apparatus of claim 16, wherein the rotation adjustment assembly includes an annular support gear, a drive pinion and a stepper motor adapted so that the stepper motor drives the pinion which in turn drives the annular support gear to rotate the cradle around an axis A.

18. The apparatus of claim 17, wherein the annular support gear includes a plurality of receivers corresponding in number and location to the plurality of corners of the cradle and each height adjustment screw includes a support tip and each support tip is received in one of the receivers in the annular support gear below the corners of the cradle.

19. The apparatus of claim 18, wherein the base includes a guide track for the annular support gear, wherein the guide track is a circular rail on an upper face of the base and the pinion rotates on a stub shaft projecting from the upper face of the base.

20. The apparatus of claim 17, wherein the controller is configured to control operation of the stepper motors of the tilt adjustment assembly and the rotation adjustment assembly.

* * * * *